United States Patent [19]
Holden, II et al.

[11] Patent Number: 5,957,910
[45] Date of Patent: Sep. 28, 1999

[54] CATHETERS WITH REINFORCED FILAMENTS

[75] Inventors: Richard W. Holden, II, Friendswood, Tex.; Anthony W. Williams, Glens Falls, N.Y.

[73] Assignee: Mallinckrodt Medical, Inc., St Louis, Mo.

[21] Appl. No.: 08/403,995

[22] Filed: Mar. 14, 1995

[51] Int. Cl.$^6$ .................................................. A61M 25/00
[52] U.S. Cl. ........................................ 604/527; 604/524
[58] Field of Search ............................ 604/280, 282, 604/264

[56] References Cited

U.S. PATENT DOCUMENTS

| | | | |
|---|---|---|---|
| 5,037,404 | 8/1991 | Gold et al. | 604/282 |
| 5,176,660 | 1/1993 | Truckai | 640/282 |
| 5,334,169 | 8/1994 | Brown et al. | 604/282 |

*Primary Examiner*—Corrine McDermott
*Attorney, Agent, or Firm*—Lawrence L. Limpus

[57] ABSTRACT

The present invention relates to catheters for use in the medical arts, and more particularly relates to such catheters having a reinforcing filament associated therewith. The catheters according to the present invention provide an improved reinforced catheter having enhanced torque characteristics.

8 Claims, 2 Drawing Sheets

CATHETERS WITH REINFORCED FILAMENTS

BACKGROUND

The present invention relates to catheters for use in the medical arts, and more particularly relates to such catheters having strengthening filaments associated therewith.

There are a number of medical procedures which are currently carried out by the use of a catheter which can be inserted into a body cavity or blood vessel of a patient. Such catheters include catheters for the localized delivery of diagnostic or therapeutic agents, catheters including one or more inflatable balloons for performing an angioplasty or similar occlusion clearing procedure, and catheters for the infusion of diagnostic or therapeutic agents over a specified region within a patient's body, as well as combinations of these catheters and others. Catheters for such medical uses are normally constructed from polymeric materials such as nylon, polyurethane, polyether polyamide blends, and other such materials. These materials provide flexibility and softness which helps to prevent damage to the patient's vessels which the catheter must traverse.

In many cases, catheters must be passed through a relatively tortious pathway such as a series of blood vessels within the patient's body so that the catheter can perform the desired function. It is therefore often desirable to have a catheter with a high degree of torquability along its length while maintaining the high degree of flexibility. One way of providing a catheter which the desired torquability is to include a reinforcing filament within the walls of the catheter.

Catheters having a reinforcing filament are known in the prior art, as shown in FIGS. 1 and 2. In particular, FIG. 1 is a plan view of a portion of a catheter, generally designated by reference numeral 10, having a number of reinforcing filaments, two of which are identified by reference numerals 20, 25. FIG. 2 is a cross sectional view of filaments 20, 25, taken at the location where the filaments 20, 25, cross each other.

Catheters may be provided with reinforcing filaments according to any one of a number of known methods. For example, in one method, an assembly of multiple spools of filament material are provided at equally spaced points around the periphery of a circular plane. This assembly is provided surrounding the exit of a standard tube extrusion machine so that the filaments may be provided during the production of the catheter. As the catheter is extruded, the assembly rotates such that a first set of spools of material provide equal and parallel spaced filaments to the catheter in a clockwise, barber pole fashion along the length of the catheter, and a second set of spools of material provide equal and parallel spaced filaments to the catheter in a counterclockwise, barber pole fashion along the length of the catheter. The first set of spools alternates with the second set of spools so that the filaments running in opposite directions cross over and under one another to form a braid pattern.

The number of spools in each set; i.e. clockwise and counterclockwise, may vary depending on the amount of reinforcing filament is desired to be incorporated within the catheter. In particular, the total number of spools may range from two to greater than fifty six. Normally, equal numbers of spools will be used for each set; i.e. clockwise and counterclockwise. However, different numbers of spools may also be used.

In a particular example, the catheter 10, is provided with the reinforcing filaments using an assembly of sixteen spools of filament material which are provided at sixteen equally spaced points around the periphery of a circular plane. As the catheter is extruded, the assembly rotates such that a first set of eight spools of material provide eight equal and parallel spaced filaments to the catheter in a clockwise, barber pole fashion along the length of the catheter, and a second set of eight spools of material provide eight equal and parallel spaced filaments to the catheter in a counterclockwise, barber pole fashion along the length of the catheter. The first set of eight spools alternates with the second set of eight spools so that the filaments running in opposite directions cross over and under one another to form the braid pattern as shown in part by FIG. 1.

The method described above places the reinforcing filaments continuously between a base coat extrusion and a top coat extrusion of the catheter. In an alternative to the above, a reel-to-reel process may be used. In this process, the base coat of the catheter is first extruded onto a mandril, the mandril being spooled off a first reel, coated with the base coat, and then spooled onto a second reel (thus the term "reel-to-reel"). Next, the reinforcing filaments are provided to the base coat in a separate reel-to-reel process using an assembly for the spools of reinforcing filaments similar to that described above. Finally, the base coat with reinforced filaments is provided with an extruded top coat using a third reel-to-reel process.

Another method of providing the reinforced filaments is to produce the catheter and the reinforced filament pattern; such as a braid, separately and then establish the filament pattern within the catheter through a series of hot die sizing processes.

Regardless of the method used, the filaments, such as filaments 20, 25, provided to the prior art catheter 10, help to increase the torquability of the catheter 10, but also allow the catheter 10, to remain relatively flexible. However, the filaments, such as filaments 20, 25, used in the prior art have a relatively large diameter, which requires the catheter 10, to have a greater wall thickness to fully surround the filaments 20, 25. The increased wall thickness; (i.e. the combination of base and top coats), increases the overall profile of the catheter 10. This means that the delivery rate capabilities of the catheter 10, will be compromised. In particular, a change of 0.002" to the inside diameter of a five french catheter can change the pressure required to deliver a specific flow of material to be delivered by as much as twenty five percent.

As noted above, the filaments, such as filaments 20, 25, are typically aligned in parallel fashion, to provide the braid pattern shown in FIG. 1. The braid pattern or density may be varied to achieve different torque characteristics and to alter the flexibility of the catheter. In particular, the denser the braid pattern, the greater the torque and the flexibility. The diameter of individual filaments, such as filaments 20, 25, are generally in the range of 0.002 to 0.004 inches and result in a catheter wall thickness in the range of 0.012 to 0.015 inches.

There remains a need in the art for improvements to braided catheters.

OBJECTS OF THE INVENTION

It is one object of the present invention to provide an improved catheter for use in the medical arts.

It is a further object of the present invention to provide an improved catheter having a longer lever arm and improved torquability within a lower profile.

It is a further object of the present invention to provide an improved catheter having a large lumen, with superior torque characteristics, and which is kink resistant.

SUMMARY OF THE INVENTION

These objects and others are accomplished according to the present invention by providing a braided catheter having at least twice the number of filaments making up the braid, but wherein individual filaments have a smaller diameter than those used in the prior art.

DETAILED DESCRIPTION OF THE INVENTION

The present invention provides an improved catheter having enhanced characteristics as noted above. The catheter according to the present invention will be discussed in detail below with reference to FIGS. 3 and 4.

Figure 3:
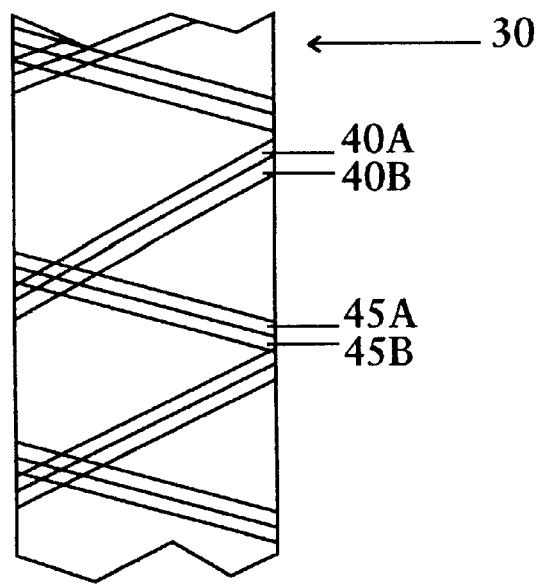
FIG. 3 is a plan view of a portion of a catheter according to one embodiment of the present invention.
Figure 4:
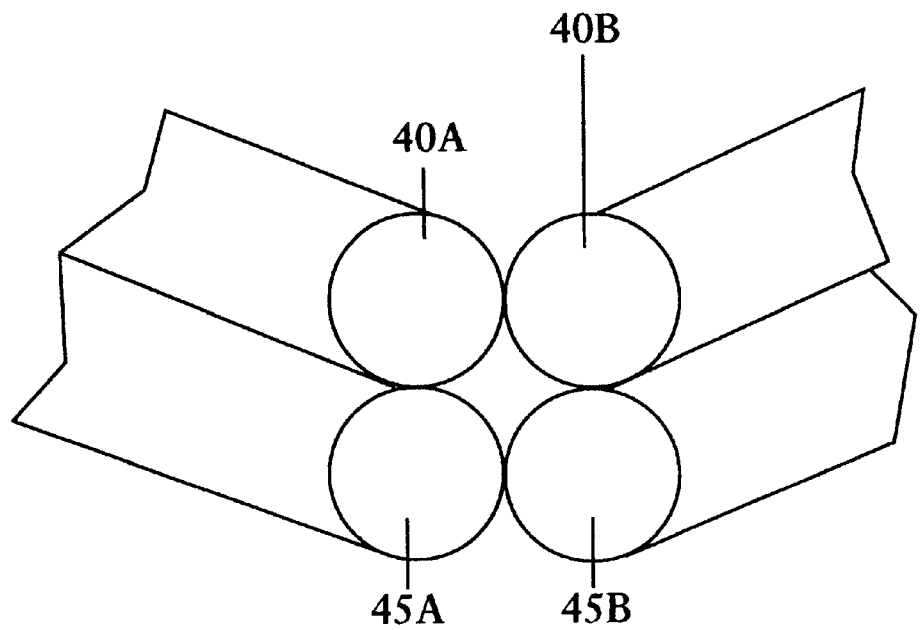
FIG. 4 is a cross sectional view of four filaments for a catheter according to one embodiment of the present invention.

FIG. 3 is a plan view of a portion of a filament reinforced catheter, typically called a braided catheter, generally designated by reference numeral 30, according to the present invention, having a reinforcing braid made up of several filaments, four of which are identified by reference numerals 40A, 40B, 45A, 45B. FIG. 4 is a cross sectional view of filaments 40A, 40B, 45A, 45B, taken at the location where the filaments 40A, 40B, 45A, 45B, cross each other.

Figure 1:
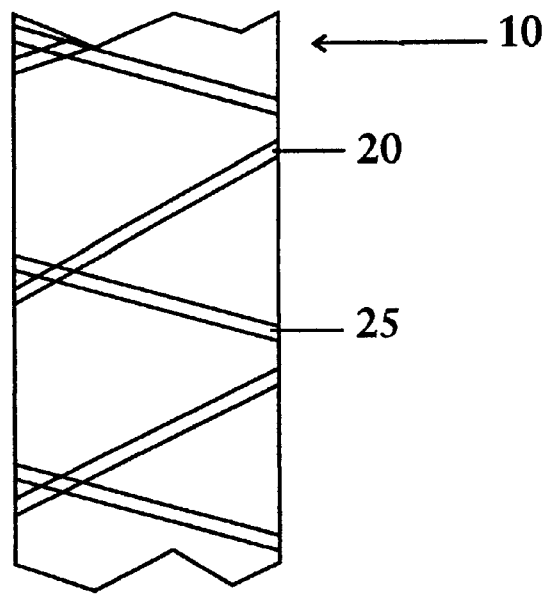
FIG. 1 is a plan view of a portion of a catheter as known in the prior art.
Figure 2:
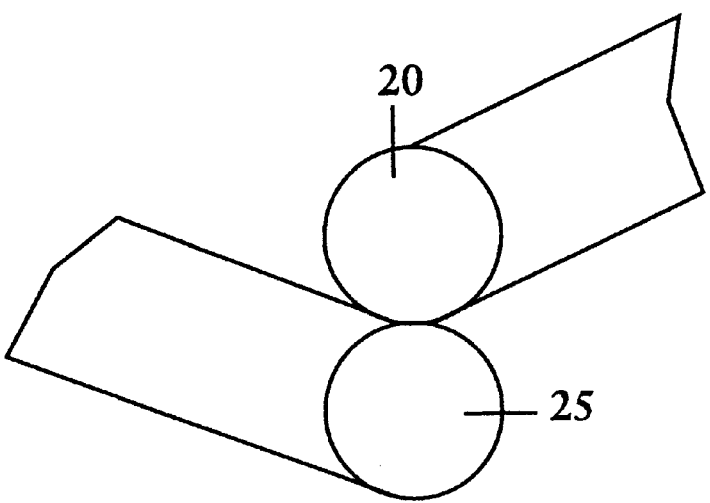
FIG. 2 is a cross sectional view of two filaments for a catheter as known in the prior art.

The catheter 30, is provided with the reinforcing filaments according to any known method, including those described above with respect to the prior art, with the exception that each spool of material includes at least two filaments having a smaller diameter than the filaments used in the prior art. These methods provide both a clockwise set of filaments and a counterclockwise set of filaments which cross over one another to form the braid pattern as shown in part by FIG. 2. It will be noted that the braid pattern of the present invention includes two filaments for every one filament of the prior art.

In a particular example, the catheter 30, is provided with the reinforcing filaments using an assembly of sixteen spools of filament material which are provided at sixteen equally spaced points around the periphery of a circular plane, wherein each spool contains two separate filaments. As the catheter is extruded, the assembly rotates such that a first set of eight spools of material provide eight pairs of equal and parallel spaced filaments to the catheter in a clockwise, barber pole fashion along the length of the catheter, and a second set of eight spools of material provide eight pairs of equal and parallel spaced filaments to the catheter in a counterclockwise, barber pole fashion along the length of the catheter. In this manner a total of thirty two filaments are provided. The first set of eight spools alternates with the second set of eight spools so that the filaments running in opposite directions cross over and under one another to form the braid pattern as shown in part by FIG. 2.

The filaments, such as filaments 40A, 40B, 45A, 45B, provide the catheter 30, of the present invention with increased torquability, but also allow the catheter 30, to remain flexible. By using the smaller filaments, such as filaments 40A, 40B, 45A, 45B, of the present invention, it is possible to provide the catheter with enhanced torque characteristics without changing the dimensions of the catheter. In addition, because the filaments, such as filaments 40A, 40B, 45A, 45B, are relatively small in diameter, the wall thickness of the catheter 30, can be less than that of comparable prior art catheters.

As with the prior art, the filaments, such as filaments 40A, 40B, 45A, 45B, filaments 40, 40', are aligned in parallel formation, to provide the braid pattern shown in FIG. 3. The braid pattern or density may be varied to achieve different torque characteristics, and to alter the flexibility of the catheter, with denser braid patterns providing greater torque and increased flexibility. The diameter of individual filaments, such as filaments 40A, 40B, 45A, 45B, are generally in the range of 0.0001 to 0.005 inches and result in a catheter wall thickness in the range of 0.005 to 0.015 inches. This is considerably less than the typical ranges known in the prior art as noted above.

The embodiment above specifically relates to the use of two filaments on each spool. However, the present invention is equally applicable to the use of more than two filaments per spool. For example, three, four or more filaments per spool may be used. The number of filaments used may be optimized in accordance with the diameter of the individual filaments to provide the enhanced characteristics for the catheter. While the multiple filaments on each spool are preferable of the same diameter, the present invention also relates to the use of two or more filaments per spool wherein the individual filaments may have the same or different diameters. Further, the spools preferably each have the same number of filaments, however, the present invention also relates to the use of different numbers of filaments on different spools. Moreover, the total number of spools may range from two to greater than fifty six. In other words, each set of spools, i.e. clockwise and counterclockwise may include from one to greater than twenty eight spools. Normally, equal numbers of spools will be used for each set; i.e. clockwise and counterclockwise; however, different numbers of spools may also be used.

In addition, FIGS. 3 and 4 show the filaments provided in a one-over-one-under braid pattern. It will be recognized that any braid pattern may be used. Further, the reinforcing filaments may be provided in any applicable pattern or manner, such as braiding, weaving, winding, etc.

The filaments of the present invention provide a number of advantages. In particular, the low profile of the filaments allows the catheter to be made with a relatively thin wall. Therefore, a catheter according to the present invention having the same outside diameter as that of a prior art catheter, can have a larger inside diameter. This in turn allows for higher flow rates of drugs or other medical solutions, to be delivered through the catheter of the present invention.

In addition, the filament reinforced catheter of the present invention has a more concentrated lever arm as well as a longer average lever arm than comparable catheters known in the prior art. As noted above, this means that a catheter according to the present invention will have greater torque capabilities than a catheter according to the prior art of similar size and construction.

The lower filament reinforcement profile of the catheters according to the present invention provide an equal or greater braid surface area to that of comparable prior art catheters and therefore has similar or greater torque characteristics. Therefore, the advantages noted above; e.g.

greater flow rates, lever arm improvements, etc., are achieved without sacrificing performance of the catheter.

The filaments may be made of any suitable high tensile transmitting materials such as stainless steel, polyaramide fibers, or similar type materials. Preferably, the filaments are stainless steel high tensile filaments.

The foregoing has been a description of certain preferred embodiments of the present invention, but is not intended to limit the invention in any way. Rather, many modifications, variations and changes in details may be made within the scope of the present invention.

What is claimed is:

1. A catheter comprising a main catheter body;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of eight equal and parallel spaced filament groups and each of said filament groups includes two or more parallel individual filaments; and wherein said second set of reinforcing filaments is comprised of equal and parallel spaced filament groups and each of said filament groups includes two or more parallel individual filaments.

2. A catheter comprising a main catheter body;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of equal and parallel spaced filament groups and each of said filament groups includes two or more parallel individual filaments; and wherein said second set of reinforcing filaments is comprised of equal and parallel spaced filament groups and each of said filament groups includes two or more parallel individual filaments; the number of filament groups in said second set of reinforcing filaments being different from the number of filament groups in said first set of reinforcing filaments.

3. A catheter comprising a main catheter body;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of equal and parallel spaced filament groups and each of said filament groups includes two or more parallel individual filaments, said individual filaments having a diameter in the range of 0.0001 to 0.005 inches; and wherein said second set of reinforcing filaments is comprised of equal and parallel spaced filament groups and each of said filament groups includes two or more parallel individual filaments, said individual filaments having a diameter in the range of 0.0001 to 0.005 inches.

4. A catheter according to claim 3, wherein individual filaments all have the same diameter.

5. A catheter according to claim 3, wherein individual filaments have different diameters.

6. A catheter comprising a main catheter body;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of equal and parallel spaced filament groups and each of said filament groups includes two or more parallel individual filaments; and wherein said second set of reinforcing filaments is comprised of equal and parallel spaced filament groups and each of said filament groups includes two or more parallel individual filaments;

said filaments being selected from the group consisting of stainless steel and polyaramide fibers.

7. A catheter comprising a main catheter body having walls having a thickness in the range of 0.005 to 0.015 inches;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of equal and parallel spaced filament groups and each of said filament groups includes two or more parallel individual filaments; and wherein said second set of reinforcing filaments is comprised of equal and parallel spaced filament groups and each of said filament groups includes two or more parallel individual filaments.

8. A catheter comprising a main catheter body made of a material selected from the group consisting of nylon, polyurethane and polyether polyamide blends;

a first set of reinforcing filaments embedded in walls of said main catheter body and extending in a clockwise manner; and a second set of reinforcing filaments embedded in walls of said main catheter body and extending in a counter-clockwise manner;

wherein said first set of reinforcing filaments is comprised of equal and parallel spaced filament groups and each of said filament groups includes two or more parallel individual filaments; and wherein said second set of reinforcing filaments is comprised of equal and parallel spaced filament groups and each of said filament groups includes two or more parallel individual filaments.

* * * * *